United States Patent
Wu et al.

(10) Patent No.: US 9,546,981 B2
(45) Date of Patent: Jan. 17, 2017

(54) DEVICE AND METHOD FOR PERFORMING BLOOD THROMBOELASTOGRAPHIC ASSAYS BY MAGNETIC SENSING

(71) Applicant: BioMedica USA, LLC, Durham, NC (US)

(72) Inventors: Jogin R. Wu, Durham, NC (US); Mario Moreno, Raleigh, NC (US)

(73) Assignee: Neotek Biosciences Co. Ltd., Suzhou, Jiangsu Province (CN)

( * ) Notice: Subject to any disclaimer, the term of this patent is extended or adjusted under 35 U.S.C. 154(b) by 0 days.

(21) Appl. No.: 13/944,616

(22) Filed: Jul. 17, 2013

(65) Prior Publication Data

US 2015/0024473 A1    Jan. 22, 2015

Related U.S. Application Data

(63) Continuation-in-part of application No. PCT/US2013/050670, filed on Jul. 16, 2013.
(Continued)

(51) Int. Cl.
*B01L 3/00* (2006.01)
*G01N 27/00* (2006.01)
(Continued)

(52) U.S. Cl.
CPC ............ *G01N 27/74* (2013.01); *G01N 11/14* (2013.01); *G01N 2011/0086* (2013.01)

(58) Field of Classification Search
CPC .. G01N 27/74; G01N 11/14; G01N 2011/0086
See application file for complete search history.

(56) References Cited

U.S. PATENT DOCUMENTS 3,766,774 A * 10/1973 Clark ........................... 73/64.42
3,798,958 A * 3/1974 Marini et al. .................... 73/10
(Continued)

FOREIGN PATENT DOCUMENTS

| CN | 101741171 | 6/2010 |
| WO | 2009047703 | 4/2009 |

OTHER PUBLICATIONS

Y.K. Mariappan et al., "Magnetic Resonance Elastography: A Review," Clinical Anatomy, 2010, vol. 23, p. 497-511.
(Continued)

*Primary Examiner* — Nathan Bowers
(74) *Attorney, Agent, or Firm* — Hamre, Schumann, Mueller & Larson, P.C.

(57) ABSTRACT

A magnetic sensor elastometry device (MSED) and a method to perform the whole blood thromboelastography assay. It contains key components, including sample cuvette, detecting head, rotating disc, optical motion detector, and etc; and measures viscoelasticity of whole blood samples. The device optically monitors the physical motion of the magnetically driven rotating disc immersed in the blood sample. The thromboelastograph is recorded by the optical motion detector reading high pulse counts through a gated time window passing through the rotating disc. The device also includes a microcontroller and its embedded firmware to perform the functions of driving the rotating magnetic disc, generating high-frequency pulses, controlling the data pulse time window, as well as handling the user's interface, data analysis, and maintaining communication with an external computer.

6 Claims, 11 Drawing Sheets

Related U.S. Application Data

(60) Provisional application No. 61/692,141, filed on Aug. 22, 2012.

(51) Int. Cl.
  *G01N 11/00* (2006.01)
  *G01N 27/74* (2006.01)
  *G01N 11/14* (2006.01)

(56) References Cited

U.S. PATENT DOCUMENTS

| | | | |
|---|---|---|---|
| 3,861,197 A | 1/1975 | Adler | |
| 4,193,293 A | 3/1980 | Cavallari | |
| 4,267,647 A * | 5/1981 | Anderson et al. | 434/301 |
| 5,229,838 A * | 7/1993 | Ganz et al. | 356/328 |
| 5,523,238 A * | 6/1996 | Varon et al. | 436/69 |
| 6,085,599 A | 7/2000 | Feller | |
| 6,208,446 B1 * | 3/2001 | Faifman | 398/136 |
| 7,207,210 B2 * | 4/2007 | Moonay | 73/54.28 |
| 2001/0049465 A1 | 12/2001 | Goldberg et al. | |
| 2003/0180824 A1 * | 9/2003 | Mpock et al. | 435/13 |
| 2005/0255601 A1 * | 11/2005 | Nippoldt et al. | 436/69 |
| 2007/0059840 A1 | 3/2007 | Cohen et al. | |
| 2008/0206880 A9 * | 8/2008 | Clague et al. | 436/69 |
| 2008/0261261 A1 | 10/2008 | Grimes et al. | |
| 2009/0055837 A1 | 2/2009 | Campbell | |
| 2009/0323741 A1 | 12/2009 | Deladurantaye et al. | |
| 2010/0154520 A1 | 6/2010 | Schubert et al. | |
| 2011/0004104 A1 | 1/2011 | Sandrin | |

OTHER PUBLICATIONS

Extended European Search Report issued for European application No. 13831497.6, dated Feb. 16, 2016 (6 pages).
International Search Report for international application No. PCT/US2013/050670, dated Nov. 7, 2013 (3 pages).
S. I. Reger et al., "A photometric coagulometer," Medical and Biological Engineering, Jan. 1976, vol. 14 (1), p. 19-24.

* cited by examiner

DEVICE AND METHOD FOR PERFORMING BLOOD THROMBOELASTOGRAPHIC ASSAYS BY MAGNETIC SENSING

The current application is a continuation in part of PCT Application Number PCT/US13/50670 filed Jul. 16, 2013 which claims benefit of U.S. Provisional Patent Application No. 61/692,141 filed Aug. 22, 2012.

FIELD OF THE INVENTION

The present invention relates generally to the blood thromboelastographic assay. More specifically, the present invention is a convenient device and method for performing whole blood thromboelastographic assay by magnetic sensing to test blood clot formation, retraction and/or lyses process.

BACKGROUND OF THE INVENTION

An accurate assessment of the efficiency of blood coagulation (thromboelastography) is very important for treating hemorrhage, trauma, as well as for various anesthetic and surgical procedures.

Coagulation is the process whereby blood forms clots. Blood coagulation, i.e., thrombogenesis, is a result of a series of biochemical reactions through primary hemostasis and secondary hemostasis. Briefly, primary hemostasis involves platelets adhesion and aggregation; secondary hemostasis involves plasma factors reacting with each other and fibrinogen being converted into cross-linked polymeric fibrin through several enzymatic reactions. Blood coagulation is the cessation of blood loss from a damaged vessel, wherein a damaged blood vessel wall is covered by a platelet and fibrin-containing clot to stop bleeding and begin the repair of damaged vessel. Disorders of this coagulation can lead to an increased risk of bleeding (hemorrhage) or obstructive clotting (thrombosis).

The coagulation usually begins almost instantly after an injury to the blood vessel has damaged the endothelium lining the vessel. Exposure of the damaged vessel wall to the bare tissue in the wound led to initiation of coagulation by tissue factor expressed as an integral membrane protein. Tissue factor binds to plasma factor VIIa initiates enzymatic reactions of procoagulant plasma proteins that lead to the formation of thrombin resulting in platelet activation and subsequent assembly of procoagulant complexes on the platelet surface leading to the conversion of fibrinogen to cross-linked fibrin clots which strengthen the platelet plug. This coagulation cascade is regulated tightly by various endogenous anticoagulants that act at different steps in the pathway to maintain the balance between clotting and bleeding.

Conventional coagulation assays have poor predictive accuracy for surgical bleeding and coagulopathy caused by traumatic injury and hemorrhage. These assays are generally performed in vitro without platelets and other blood cells; and also not able to test hemostasis function for hypothermic patients. With these conventional approaches, the pathophysiology of bleeding associated with trauma coagulopathy and of massive intraoperative blood loss cannot be clearly differentiated, thus making substitution of blood products difficult. Trauma is one of the leading causes of death worldwide. Hemorrhage is responsible for 40% of trauma caused deaths. Coagulopathy associated with severe injury complicates the control of bleeding and is linked to the increased morbidity and mortality in trauma patients. Rapid diagnosis and directed interventions may reduce preventable deaths after severe injury. The causes of coagulopathy in patients with severe trauma are multifactorial, including consumption and dilution of platelets and coagulation factors, as well as dysfunctions of platelets and the coagulation system. Hypothermia, acidosis, and dilution from standard resuscitation can worsen the presenting coagulopathy and perpetuate bleeding. Strategies to prevent significant coagulopathy and to effectively control critical bleeding in the presence of coagulopathy may reduce the requirement for blood transfusion, thereby improving clinical outcome of patients with major trauma.

In addition, the hemorrhage in traumatized casualties remains the major cause of death in combats. A rugged device to assess overall hemostasis function in forward combat areas is thus strongly desired. Also, perioperative diagnosis and monitoring of blood coagulation is critical to better understand the causes of hemorrhage, to guide hemostatic therapies, and to predict the risk of bleeding during the consecutive anesthetic or surgical procedures. For patients undergoing major surgery, or under urgent situations such as trauma, hemorrhage, stoke or sepsis, a timely informed blood coagulation assessment is critically needed in determining patient susceptibility to postoperative thrombotic complications or as indicator of early sepsis, particularly regarding the use of blood products and guiding treatment with haemostatic components.

Concerning the test of thromboelastography, usually a small sample of blood (typically 0.36 ml) is placed into a cuvette that is rotated gently through 4° 45' (cycle time 6 min) to imitate sluggish venous flow and activate coagulation. When a sensor is inserted into the sample, a clot will form between the cuvette and the sensor. The speed and strength of the clot formation can be measured in various ways; and are dependent on the activity of the plasmatic coagulation system, platelet function, fibrinolysis and other factors which may be affected by illness, environment and medications. If there is suspicion that the blood has difficulty to clot due to either medication or disease, the blood sample would be exposed to a clot-inducing agent (such as kaolin) immediately prior to the test.

The first thromboelastography method was introduced by Hartert in 1948 and certain modifications have been made over the years to improve the technique. Hartert introduced a cylindrical member rigidly mounted in the solid frame and a beaker mounted on the upper end of a rod-like support that is mounted onto the solid frame by means of a circular resilient diaphragm. A coil arrangement at the lower end of the rod produces a rotating electro-magnet field and imparts to the rod an orbital movement. A further core above the diaphragm is used as the pick-up device to record trace of the change in amplitude of the elastic support upon clot formation. This allows more detailed and accurate recording of the clot formation process. Haemoscope Corporation further improves the technique and includes a torque sensing column and a drive ring disposed around a body of the column. The apparatus further includes a first guide shaft rigidly secured to the drive ring and a cup holder. This invention led to the current Haemoscope TEG device.

Advances in technology have led to certain developments of thromboelastography techniques. The TEG® device (Haemoscope Corporation, IL, USA) and ROTEM® device (Pentapharm Gmbh, Germany) both measure clot viscoelasticity and provide the rate, strength and stability of clot formation, as well as fibrinolysis process in patients at perioperative clinical settings to guide resuscitation particularly regarding to the use of blood products. However, current TEG® and ROTEM® technologies both use fragile moving parts (either a rotating pin or a rotating cup) and sophisticated mechanical assemblies which made the devices difficult to use at a point-of-care setting or in combat areas under war conditions. The detection signals used in the current TEG® and ROTEM® technology are obtained either by torsion wire or by light change reflected on a moving mirror. Disadvantages of the current TEG® or ROTEM® technology also include low precision, low sensitivity (signal-to-noise ratio), and interference from vibration, limited transportability and difficulty of handling whole blood samples.

Other techniques have also been developed to detect blood elasticity changes upon clot formation. Among them, the Sonoclot Analyzer (Sienco Inc., Arvada, Colo.) uses a hollow, open-ended disposable plastic probe mounted on a transducer head where the probe oscillates vertically during testing. The changes in impedance to movement imposed by the developing clot are recorded. However the Sonoclot test trace has been considered as rather qualitative in its clinical applications.

Moreover, the maximal clot firmness of these techniques is about 50 to 70 mm. Considering that a general sensitivity level is about 2 mm, higher test-to-test variations are almost unavoidable. This is a serious problem, especially in the case of measuring samples in thrombocyte inhibited tests for fibrinogen abnormality.

So far there is not a simple, reliable and rapid diagnostic test that allows clinicians to manage massively transfused blood accurately at the bedside, and to timely monitor hemostasis status, to effectively manage the associated bleeding and make correct diagnosis and optimal use of blood products.

It is therefore an objective of the present invention to provide a quick and easy device and method for performing blood thromboelastographic assay, particularly measuring blood clot formation, rate of clot formation, clot strength and degree of blood fibrinolysis.

DETAIL DESCRIPTIONS OF THE INVENTION

Figure 1:
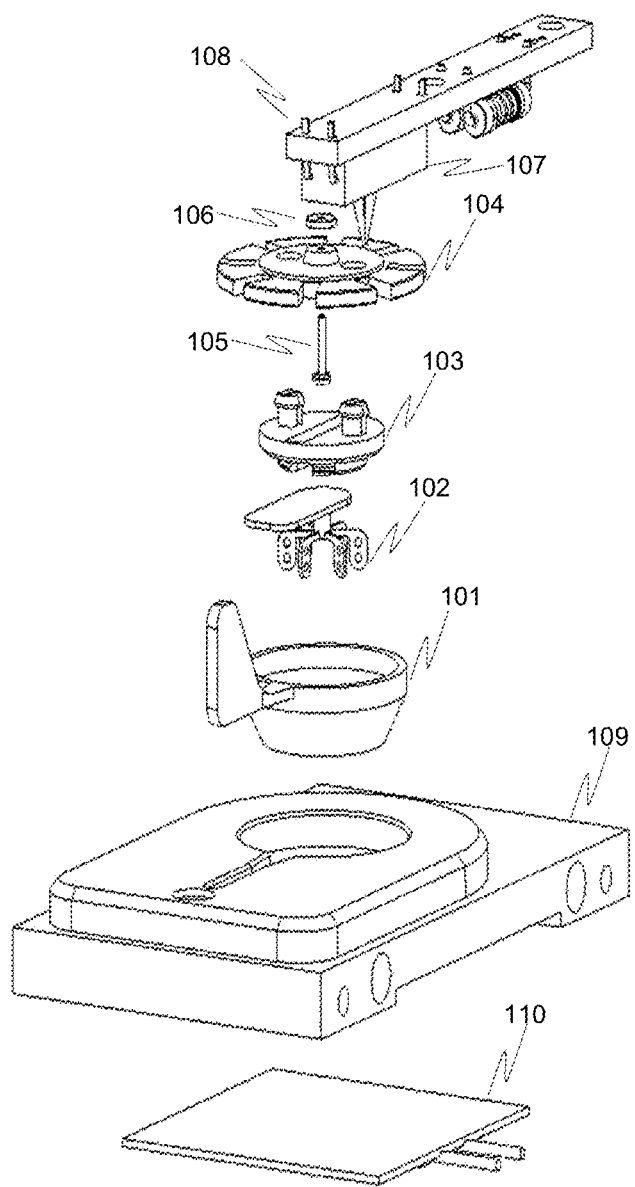
FIG. 1 depicts a preferred embodiment of the present invention with an exploded view of the detection sub-assembly.
Figure 2:
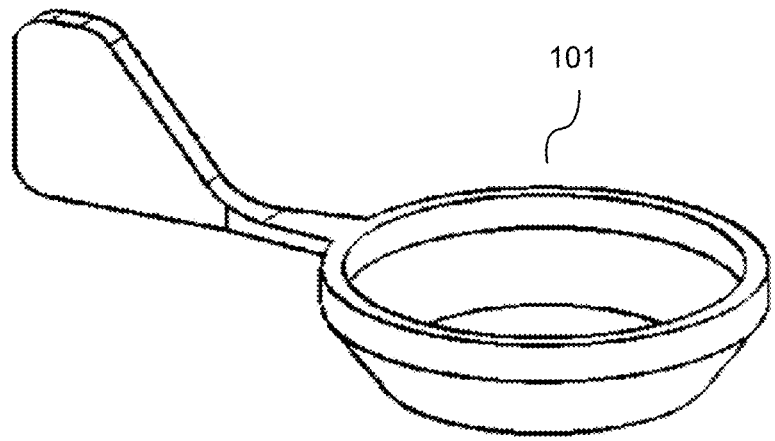
FIG. 2 depicts an embodiment of a sample cuvette.
Figure 3:
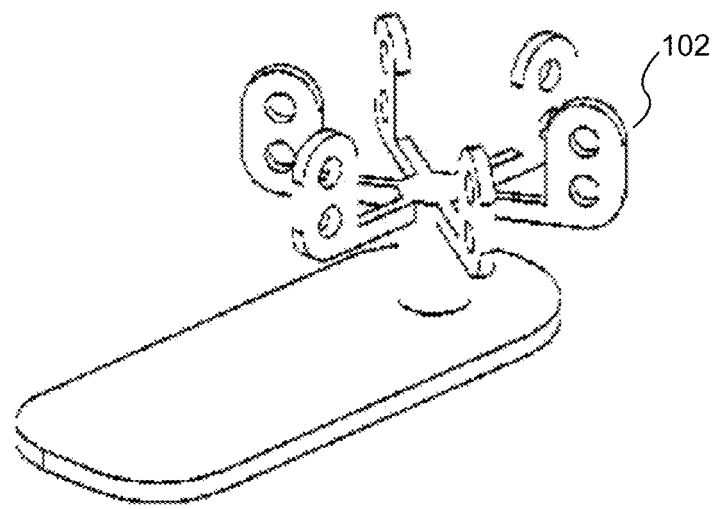
FIG. 3 depicts an embodiment of a detection head.
Figure 4:
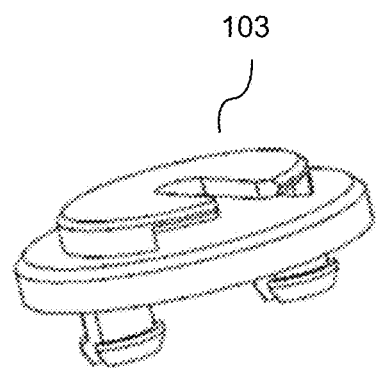
FIG. 4 depicts an embodiment of a coupling/receiving cavity.
Figure 5:
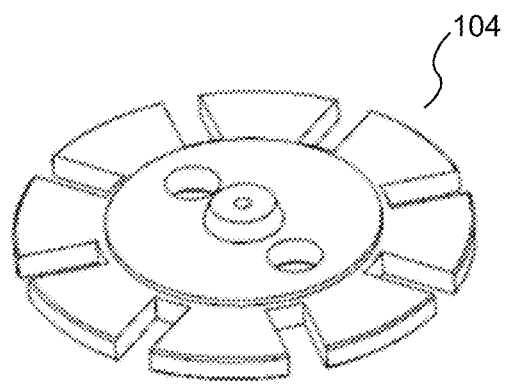
FIG. 5 depicts an embodiment of a rotating disc.
Figure 6:
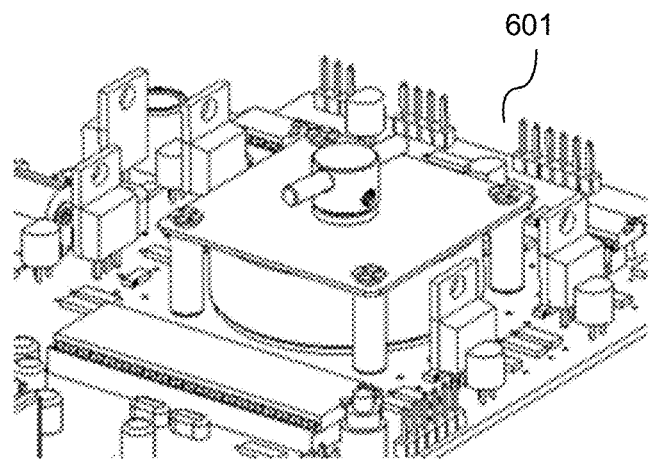
FIG. 6 depicts an embodiment of a stepper-based electro-mechanical rotary magnetic field generator.
Figure 7:
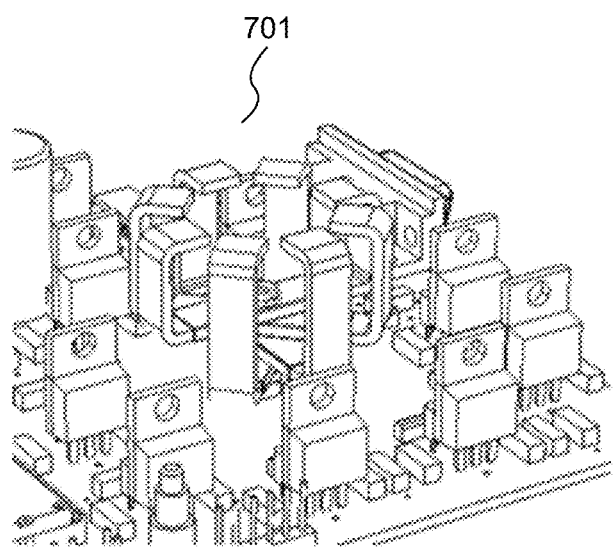
FIG. 7 depicts an embodiment of a static coils-based electro-mechanical rotary magnetic field generator.
Figure 8:
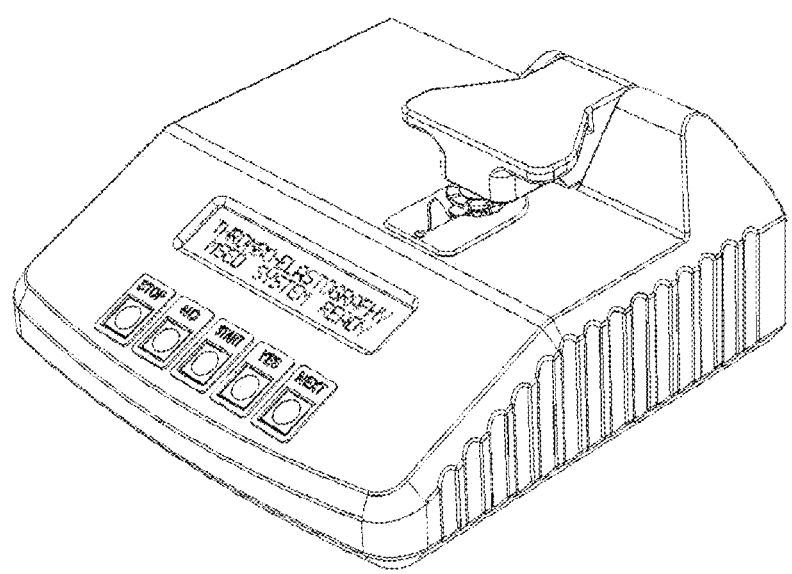
FIG. 8 is an isometric view of the present invention.
Figure 9:
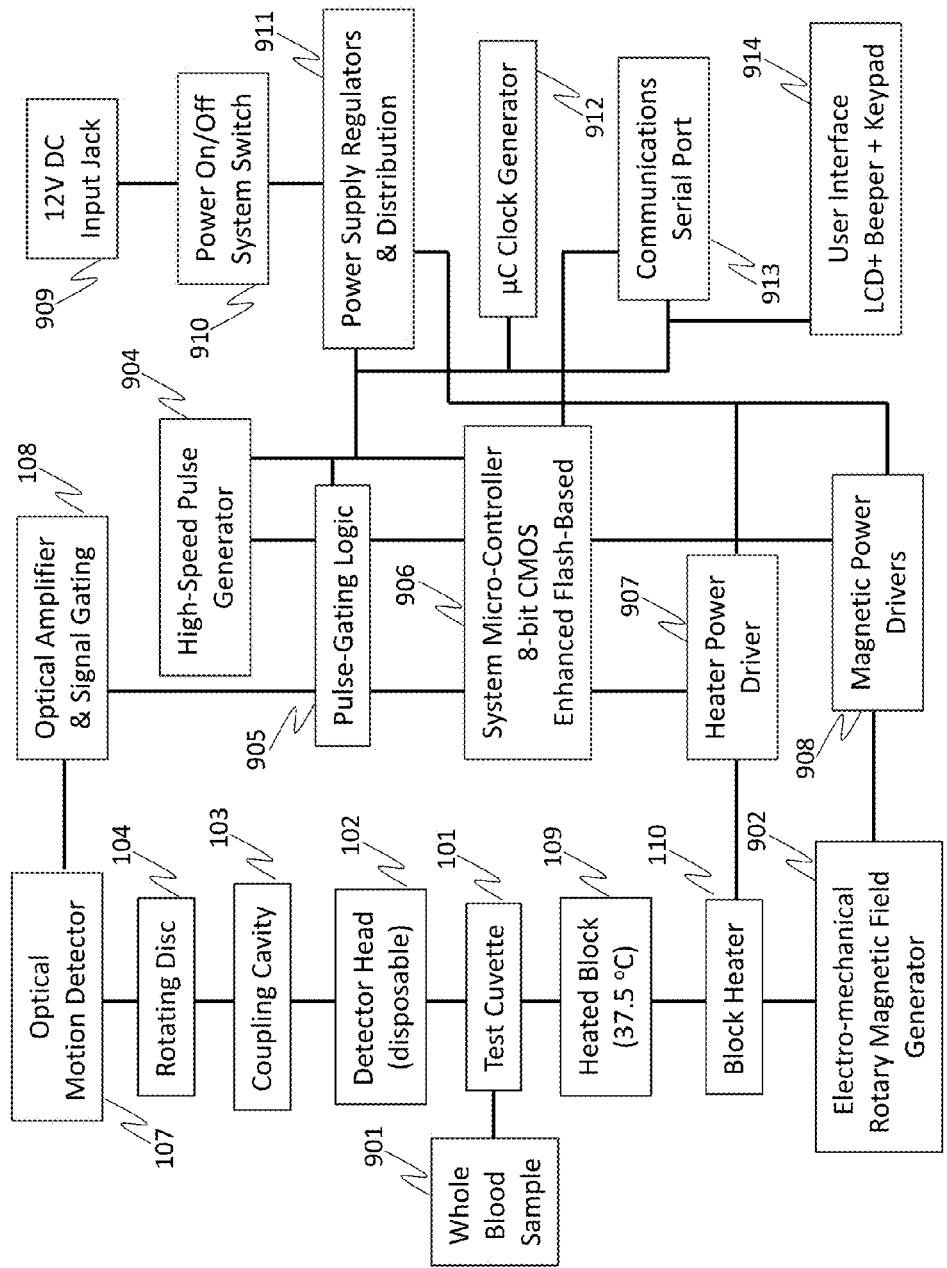
FIG. 9 is a block diagram of the basic system and dedicated electronics.

All illustrations of the drawings and descriptions of the embodiments are for the purpose of describing selected versions of the present invention and are not intended to limit the scope of the present invention.

The present invention relates to a device and method for performing whole blood thromboelastography assays. It is also related to a portable device that is easy to use, accurate, and quick for testing a patient's blood at bedside, physician's office, operating room, or even in battle field. The present invention, a Magnetic Sensor Elastometry Device (MSED), measures the viscoelasticity properties of whole blood. During the test, once the coagulation cascade is activated, whether through the intrinsic pathway, extrinsic pathway or a combination of both, thrombin is formed. The thrombin cleaves soluble fibrinogen into fibrin monomers, which spontaneously polymerize to network of cross-linked fibrin. A unique property of this network structure is that it behaves as a rigid elastic solid, capable of resisting deforming shear stress of flowing blood.

It is an objective of the present invention to provide a device for performing blood thromboelastography assays of, particularly but not limited to, onset of clotting time, rate of clot formation, clot strength, degree of fibrinolysis process. Parameters that guide blood product use and/or drugs used during operation are also the applications of the present invention.

It is further an objective of the present invention to use a sample cup and a rotating disc coaxially oriented. The deforming shear stress initiated by the rotating disc immersed in the test blood sample is detected and measured at its own body (at the rotating disc).

It is further an objective of the present invention to provide means of controlling and balancing the deforming stress and the resisting force of whole blood fibrin network in order to measure the true viscoelasticity changes upon blood clot formation.

It is yet further an objective of the present invention to provide means of detecting the resistance of blood clot with an accurate sensing technique with minor mechanical interference, e.g., an optical reader using gating technique in high pulse mode for data counting.

The present invention comprises a sample cuvette sitting in a sample holder heated by a heated block to provide constant temperature at 37° C., a rotating disc and a detection head coupled by a docking cavity, a magnetic field generator providing means for the rotating disc, a disc shaft and a shaft locking pin to secure the rotating disc, a crystal timer and an optical reader together with optical amplifier and signal gating circuit.

A detection head, made of plastic material, is inserted into a rotating disc through a coupling cavity. When the assembly is immersed into a sample cuvette, a reagent is added to trigger the hemostasis process. A proprietary microcontroller and its embedded firmware perform the functions of driving the magnetic rotating disc back and forth at a predetermined speed, generating high-frequency pulses at the optical reader, controlling the time window for collecting pulse counts, reading the optically-gated data from the rotating disc to obtain the trace of thromboelastograph, and so on. Other extended implementations of the present invention will also enable the ability to run multiple blood samples and/or assays simultaneously.

In reference to FIGS. 1 to 9, an embodiment of the present invention consists of a sample cuvette 101, a detection head 102, a rotating disc coupling and receiving cavity 103, a rotating disc 104, a magnetic field generator 902, including stepper-based electro-mechanical rotary magnetic field generator 601, and static coils-based electro-mechanical rotary magnetic field generator 701. FIG. 1 is an exploded view of the detection sub-assembly, including: (1) cuvette 101 (to hold the blood sample under test), (2) detection head 102, (3) rotating disc coupling and receiving cavity 103, (4) rotating disc 104, (5) disc shaft 105, (6) shaft locking pin 106, (7) optical reader 107, (8) optical amplifier and signal gating circuit 108, (9) heated block 109 to provide constant temperature at 37° C., (10) electro-mechanical rotary magnetic field generator 601 and 701, and (11) block heater 110.

In the present invention, the viscoelasticity of blood hemostasis may be measured by placing a detection head 102 in contact with the whole blood sample 901 placed in a sample cuvette 101. The blood's temperature is maintained at 37° C. with the aid of a computer controlled heated sampling bay. The detection head 102 is temporarily attached to the rotating disc 104 via a coupling mechanism of the coupling and receiving cavity 103. The rotating disc is then moved by the magnetic rotating field underneath the cuvette holding unit. Initially, the detection head/rotating disc assembly follows instantly, with no perceptible delay, the magnetic rotary motion. As time lapses, once coagulation reagent added into the sample, blood sample's viscoelasticity changes during the process of clot formation, and the detection head/rotating disc assembly motion response changes, exhibiting a slowing speed proportional to the current blood viscoelasticity. Such process continues through certain time allowing the blood to reach the highest viscoelasticity change, and barely permitting the detection head/rotating disc sub-assembly to follow the magnetic rotary motions. Under this condition, the rotating disc 104 will continue to move, but the speed of its motion will be reduced proportionally to the viscoelasticity level reached by the blood sample under test.

Figure 10:
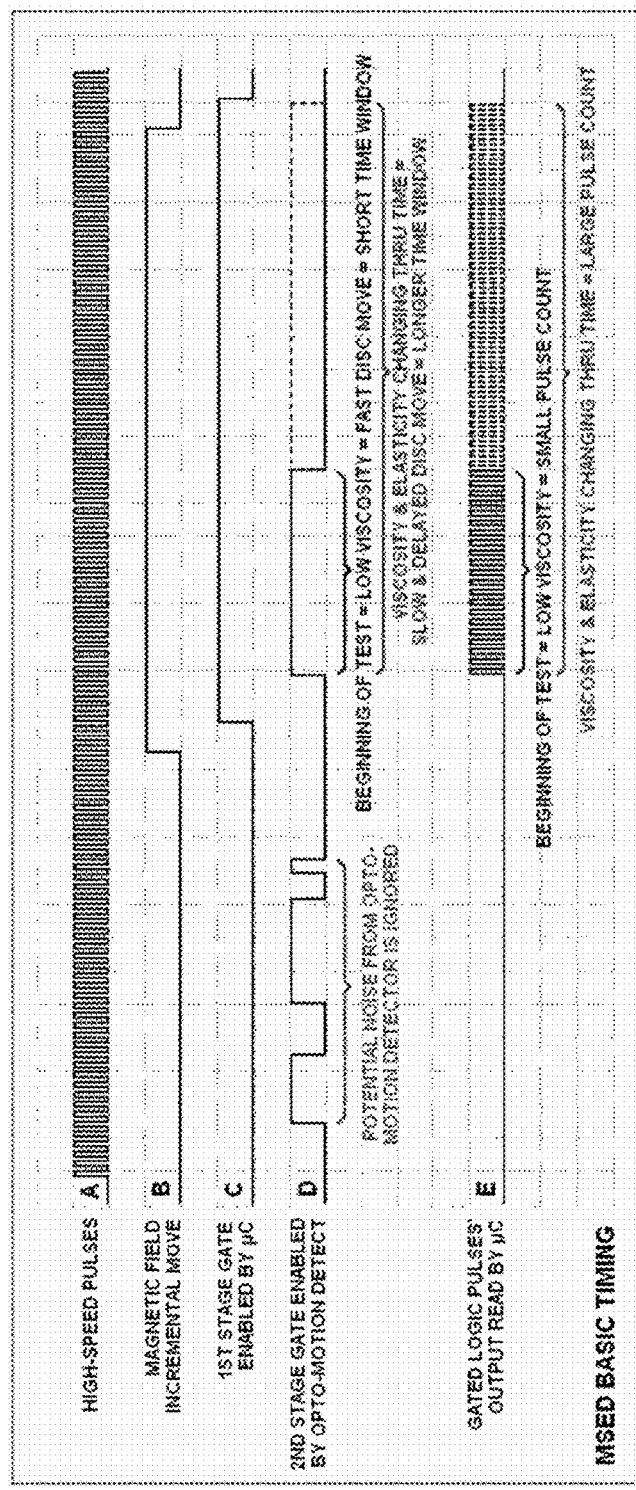
FIG. 10 is a waveform chart demonstrating the detection front-end basic timing.
Figure 11:
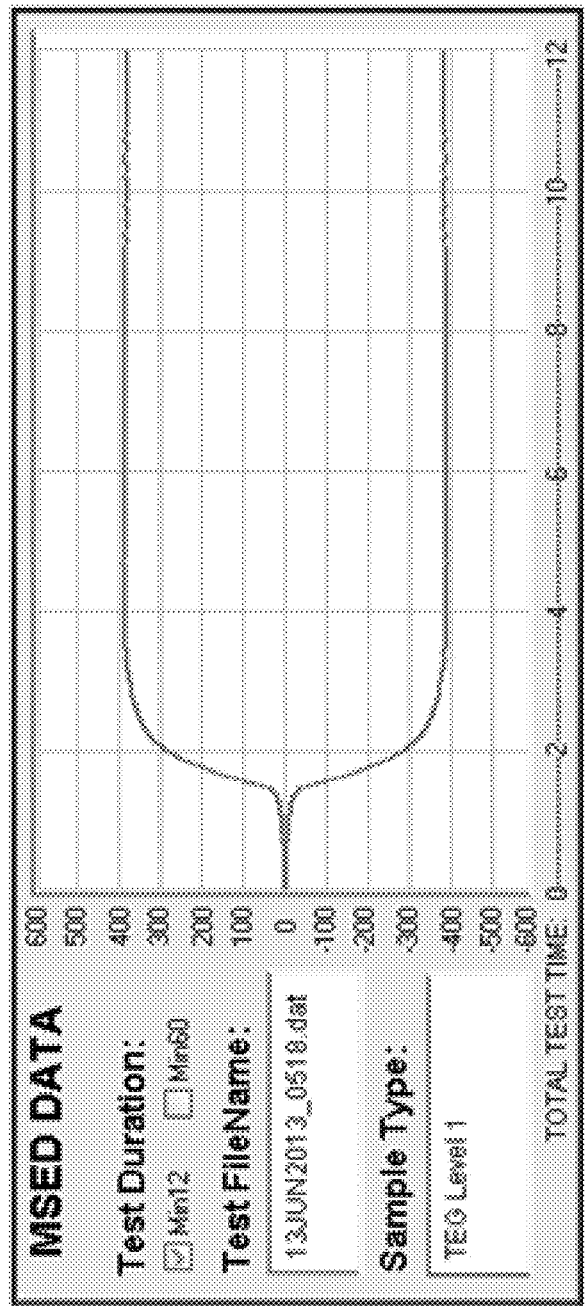
FIG. 11 is a typical trace of thromboelastograph for "TEG Level-1".
Figure 12:
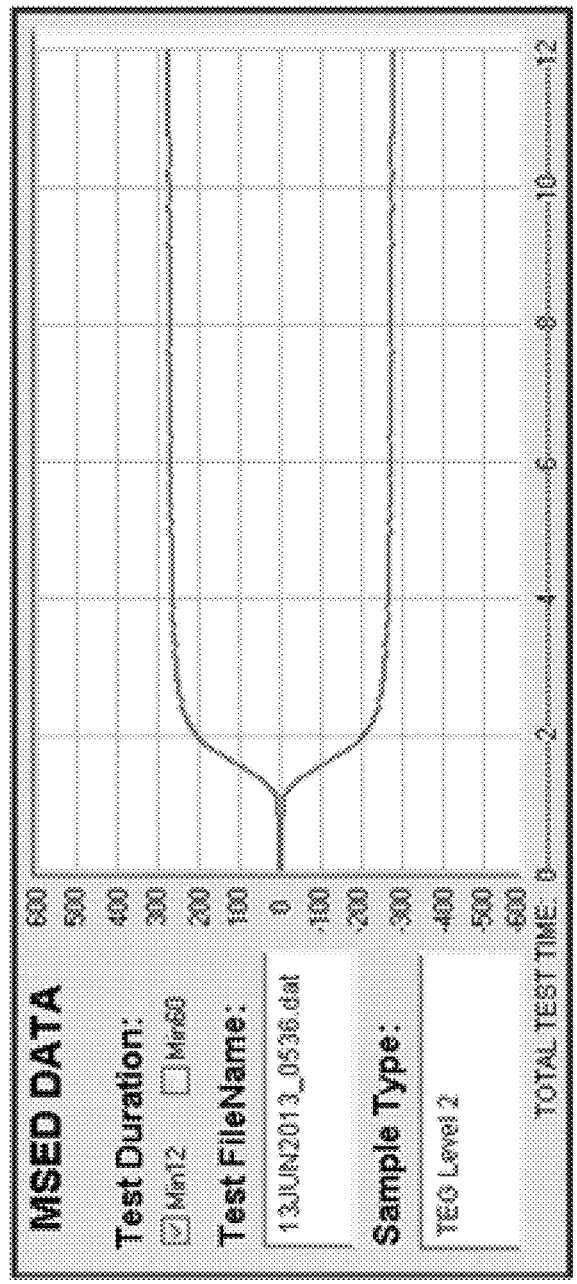
FIG. 12 is a typical trace of thromboelastograph for "TEG Level-2".

This device uses the combination of a cylindrical cup and a matching shear-inducing disc, and uses an optical gating assembly allowing accurate signal collection following the viscoelasticity changes upon blood clot formation. In one embodiment of the invention, the system uses a new and unique approach to detect the viscoelasticity characteristics of the testing sample. This novel method exploits the electro-mechanical motion parameters and the physical changes of the whole blood sample following the addition of a reagent. At beginning of the test, the high-speed pulse generator is running (FIG. 10-A), the system microcontroller 906 energizes the magnetic power drivers 908 which produce incremental rotational movement of the rotating disc 104 and detection head 102 (FIG. 10-B). The rotating disc 104 has an angular rotation range of 45 degrees comprising a number of angular motions equally spaced (for example, 3 equal angular motions of 15 degrees each; or 6 equal angular motions of 7.5 degrees each). At the same time, the microcontroller 906 enables the first stage of the pulse-gating logic (FIG. 10-C), permitting the high-speed pulses to pass through. The optical reader 107 monitors the rotating disc 104. The amplified output enables or disables the second gate (FIG. 10-D) of the high-speed pulses; which will be read by the microcontroller 906 (FIG. 10-E). The optical reader 107 will produce a "time window" directly proportional to the speed at which the rotating disc 104 is rotating and the time delayed response of the rotating disc. Therefore, right at the moment when the reagent is added to the whole blood sample 901, the liquid mixture exhibits the lowest viscoelasticity values; and the response of the rotating disc 104 is almost instantaneous with no perceptible time delay. Thus the "gated time window" is very short, permitting only a small number of high-speed pulses generated by high-speed pulse generator 904 to pass through. As time goes by, the viscoelasticity of the testing sample changes; and this forces the rotating disc 104 to slow down its rotational speed and starts causing time response delays. So, among the multiple-stage gated time windows for reading, the first gated time window is enabled by the microcontroller 906; and the second gated time window is controlled by a rotating angular speed of the rotating disc 104. As a result, the "gated time window" becomes longer, and allows larger number of pulses to pass through. Several default conditions were setup when this invention was reduced to practice, including the frequency of the high-speed pulse generator 904, the width of the slots on the rotating disc 104, the angle and width of the optical beam, the time allotted to the microcontroller 906 to read the incoming pulses, and the optimal rotational magnetic speed which was set as 1,875 milliseconds per incremental angular move.

In addition, a thromboelastography reagent is used for causing controlled viscoelasticity changes of the blood sample held in the sample cuvette 101. The reagent is calcium chloride, either a lyophilized reagent or an air-dried reagent. Moreover, the thromboelastography reagent may also include kaolin, tissue factor, heparinase, platelet inhibitor, or aprotinin.

In one embodiment of the present invention, the processing electronic components are shown in the system block diagram (FIG. 9) as follows: a power supply, fed by an external AC to DC power adapter and equipped with voltage regulators and distribution 911; an optical reader 107; an optical amplifier and signal gating 108; a high-speed pulse generator 904; a pulse-gating logic 905; a heater's power driver 907; a block heater 110; a set of magnetic power drivers 908; a microcontroller's clock generator 912; an 8-bit CMOS enhanced flash-based system microcontroller 906; a serial communications port 913; a 12V DC input jack 909; a user interface 914 comprising an ON/OFF power switch 910, an LCD screen, a audible beeper and a keypad. A full system may also include an external or internal computer.

When the device is powered up, the system microcontroller 906 will perform the following actions in order: 1) Immediate disable of all power drivers, for safety and minimizing power consumption; 2) User interface initialization: LCD, beeper and keypad; 3) Display startup message; 4) Internal self-test for firmware integrity; 5) Display self-test results if any errors are found and wait for operator's acknowledge; 6) Display welcome message and firmware version number; 7) Wait for operator's input; 8) Monitor cuvette bay (heated block) for proper operating temperature; 9) Monitor communications port; 10) Display "System Ready" prompt when a predetermined test temperature is reached; 11) Wait for operator's input command (s); 12) Guide operator through the test procedure via LCD messages; 13) Monitor Detection Arm position; 14) Run thromboelastometry test; 15) Acquire and transmit sensor raw data via serial communications port; 16) Calculate, store and display results; and 17) Wait for operator's input.

In one embodiment of this invention, the whole blood sample volume is 260 micro-liters along with 40 micro-liters of the reagent. In particular, the whole blood thromboelastometry test is performed following these steps: 1) The device is powered-on; 2) Welcome message and firmware version number are displayed on the LCD; 3) The system running an auto self-test; 4) Checking the testing bay (cuvette heating block) for the correct temperature; 5) Once the temperature is reached, the 'ready' message being displayed; 6) The system instructing the operator to lift the detection arm; 7) Promoting to insert a detection head; 8) Placing a cuvette in the testing bay; 9) Instructing to deliver the whole blood sample into the cuvette; 10) Waiting for the blood sample to reach the proper test temperature; 11) Once the sample reaches 37° C., the operator being instructed to deliver the reagent; 12) Starting test and data being collected and sent to main computer; 13) The MSED device displaying a message to indicate the test has ended; 14) The raw data received by the computer being stored for future access; 15) A graphical corresponding curve appearing on the computer screen; 16) Post-processing algorithms (base-line subtraction, multi-point smoothing filters, and bipolar graphing) being applied for further evaluation and final test analysis; and 17) The total testing times can be set as: 12, 24, 36, and 60 minutes.

In reference to FIGS. 11-14, certain exemplary examples were presented. Exhaustive studies revealed that at the beginning of testing the 'TEG Level-1' samples, the number of pulses was typically low (about 70 per read) and went up to a higher number of pulses (about 470 pulses per read) as the maximum viscoelasticity was reached through the test. The data-handling algorithm treated the initial numbers as a baseline, and reduced all data points by subtracting those baseline numbers from all acquired data points, to produce a data curve that showed values between 1 and 400 (FIG. 11), and reaching the maximum amplitude in 2 minutes. Additional testing was performed using 'TEG Level-2' samples. It was observed that the initial values were slightly lower than those obtained with the Level-1 sample, roughly 55 per read and roughly 345 per read as the maximum viscoelasticity was reached. Once the baseline subtraction was applied, the resulting curve showed values between 1 and 290 (FIG. 12), with the maximum amplitude detected in 6 minutes.

Figure 13:
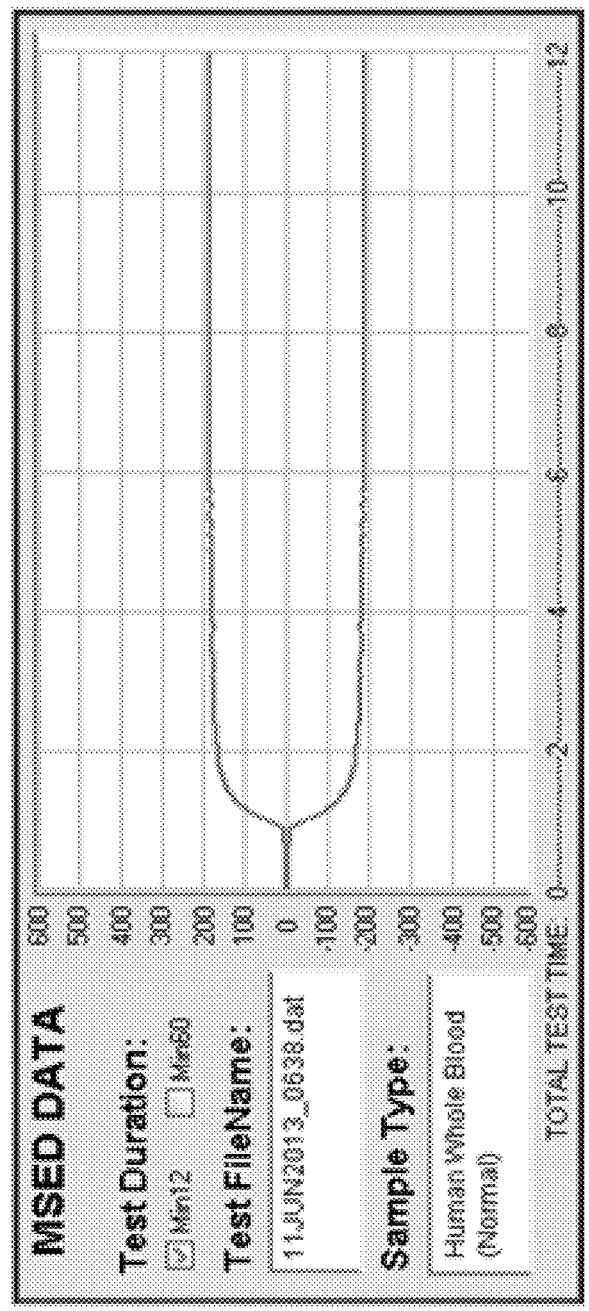
FIG. 13 is a typical trace of thromboelastograph for normal human whole blood.
Figure 14:
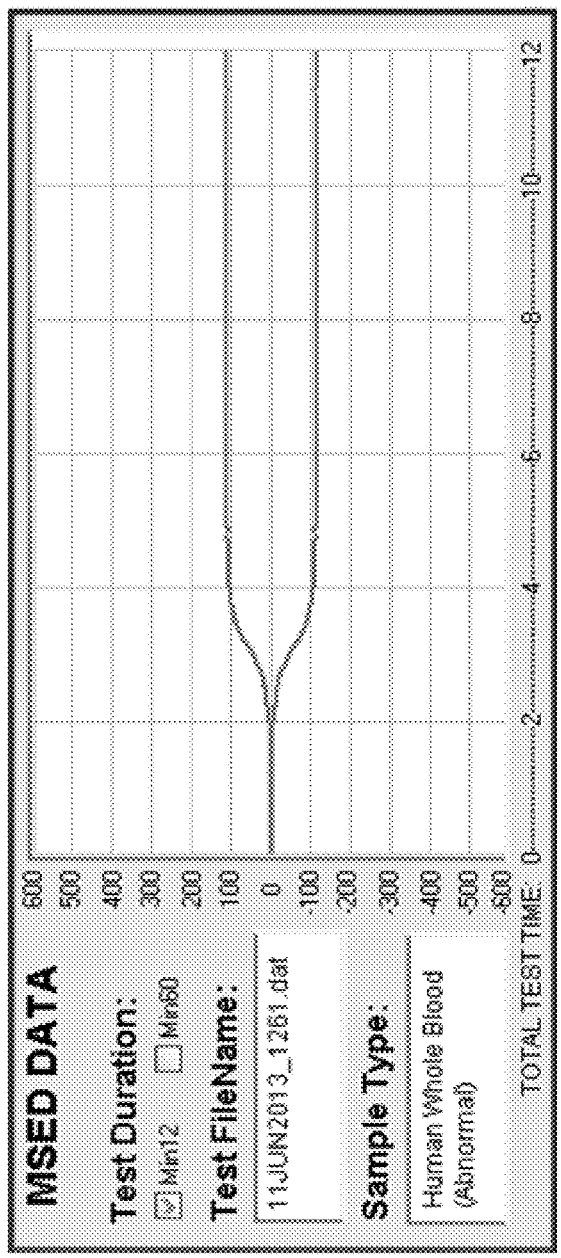
FIG. 14 is a typical trace of thromboelastograph for abnormal human whole blood.

In the next study using normal human whole blood samples, the initial baseline number of pulses was typically low, roughly 80 per read. The obtained high number of pulses was roughly 280 pulses per read, as the maximum amplitude was reached through the test. The baseline subtraction was also applied. The resulting curve showed values between 1 and 200 (FIG. 13). Subsequent testing was performed using abnormal human whole blood sample that had low plasma factor levels and low platelet counts as compared with normal human blood. It was observed that the initial values were slightly lower than those obtained with normal human whole blood samples, roughly 65 per read. The value reached roughly 165 per read as the maximum amplitude was reached. After the baseline being subtracted, the resulting curve showed values between 1 and 100 (FIG. 14). As whole blood and the TEG L1 and L2 samples having different matrix effect, current experimental set up was not optimized for whole blood samples to reach maximum sensitivity at this point. In these tests, both detection head and cuvette were disposable elements to be discarded after each individual test.

The present invention has advantages over the existing techniques with its higher signal-to-noise ratio and higher precision. It is also sturdy and durable as compared with those wire-cup and pin-cup devices, as well as provides a broader testing range. Further, it has eliminated certain problems associated with previous devices by measuring the changes in blood elastic and viscous properties using an optically-gated time-domain window, which practically has no inherent noise.

The present invention utilizes a sensor comprising a detection head and rotating disc sub-assembly. However, the rotational motions could be limited to predetermined angular displacement not completing a full revolution range. Moreover, the monitoring optical window can also be achieved by other technology means, such as digital encoding, angular reflectometry, full motion picture comparative analysis, etc. Other embodiments may combine the capabilities of both microcontroller and internal or external computer into either a microcontroller or a computer, making it unnecessary of the use of both.

At the time when the present invention was made, microcontroller's firmware has (in addition to running the actual biological test) the task of guiding the operator/user through each of the steps necessary to perform the complete process of whole blood testing and handle the user's response/input. It is also possible to eliminate all those in favor of a fully automated and optimized "one key press" process.

Although the invention has been explained in relation to its preferred embodiment, it is to be readily understood that many other possible modifications and variations can be made without departing from the spirit and scope of the invention as hereinafter claimed.

What is claimed is:

1. A magnetic sensor elastometry device for performing whole blood thromboelastography assays of a whole blood test sample in the process of hemostasis over time, the device having a detection system for increased sensitivity, the detection system comprising:
   a high speed electronic pulse generator that generates high speed electronic pulses at a default frequency, the high speed electronic pulse generator adapted to be enabled at a beginning of a test;
   an optical reader that uses a gating technique to read a light beam sent toward the optical reader, using a microcontroller with gating logic in high pulse mode to generate a gated time window;
   a rotating disc positioned between the electronic pulse generator and the optical reader, the rotating disc having a plurality of physical gates which allow light beams sent toward the optical reader to generate the gated time window when each gate is positioned directly between the sent light and the optical reader, such that the gated time window is directly proportional to an angular speed at which the rotating disc is rotating, wherein the high speed electronic pulses are counted during the gated time window,
   wherein the slower the rotating disc rotates, the longer the gated time window is, thus more high speed electronic pulses are counted per unit of time, wherein an increase in high speed electronic pulses over the gated time window per unit of time is proportional to an increase in viscoelasticity of the whole blood test sample;
   a cylindrical cup and a matching shear-inducing disc for holding the whole blood test sample in the process of hemostasis; and
   a heating element for holding the blood sample at a constant temperature.

2. A magnetic sensor elastometry device according to claim 1, wherein the gate on the rotating disc allowing light to pass through is one or more slots on the disc designed to pass a high speed pulse therethrough.

3. The magnetic sensor device according to claim 2, wherein there are 2 or more evenly spaced slots.

4. The magnetic sensor device according to claim 1, wherein an angular displacement of the rotating disc is an amount that is not a full revolution.

5. The magnetic sensor device according to claim 1, wherein the rotating disc is driven back and forth.

6. The magnetic sensor device according to claim 1, wherein the high speed electronic pulse generator generates the pulses independently of the optical reader and the rotating disc.

* * * * *